US006611704B1

(12) United States Patent
van Best et al.

(10) Patent No.: US 6,611,704 B1
(45) Date of Patent: Aug. 26, 2003

(54) APPARATUS FOR MEASURING THE AUTOFLUORESCENCE OF THE CORNEA OF AN EYE

(75) Inventors: Jasper Anton van Best, Leiden (NL); Franco Docchio, Brescia (IT)

(73) Assignee: Leiden University (Medical Center), Leiden (NL)

( * ) Notice: Subject to any disclaimer, the term of this patent is extended or adjusted under 35 U.S.C. 154(b) by 0 days.

(21) Appl. No.: 09/508,319

(22) PCT Filed: Oct. 9, 1998

(86) PCT No.: PCT/NL98/00525

§ 371 (c)(1), (2), (4) Date: Jul. 27, 2000

(87) PCT Pub. No.: WO99/12467

PCT Pub. Date: Mar. 18, 1999

(30) Foreign Application Priority Data

Sep. 11, 1997 (NL) ............................................ 1007011

(51) Int. Cl.[7] ................................................ A61B 6/00
(52) U.S. Cl. ........................................... 600/476; 606/1
(58) Field of Search ......................... 351/219; D24/150, D24/107; 250/462.1; 606/1; 600/476

(56) References Cited

U.S. PATENT DOCUMENTS 4,569,354 A * 2/1986 Shapiro et al. ............ 128/665
5,433,197 A * 7/1995 Stark .......................... 128/633
5,885,224 A * 3/1999 Yoshida ...................... 600/558
6,013,034 A * 1/2000 Vaz et al. ................... 600/476
6,053,614 A * 4/2000 Kawamura et al. ......... 351/211
6,276,798 B1 * 8/2001 Gil et al. .................... 351/206

* cited by examiner

*Primary Examiner*—Marvin M. Lateef
*Assistant Examiner*—Devaang Shah
(74) *Attorney, Agent, or Firm*—Robert D. Katz; Cooper & Dunham LLP

(57) ABSTRACT

For the early detection of blindness-causing diabetic retinopathy, an apparatus for measuring the autofluorescence of the cornea of an eye, comprising means for tangentially illuminating the cornea, means for receiving the autofluorescent radiation generated in the cornea by this illumination, and means for processing the measured autofluorescent radiation, wherein the means for tangentially illuminating the cornea comprises at least one light source which radiates blue light and at least one filter which transmits at least a part of the blue light in a light path to the cornea, and the means for receiving the autofluorescent radiation generated in the cornea comprises at least one filter which transmits green light.

12 Claims, 5 Drawing Sheets

RELATIVE CORNEAL EXCITATION EFFICIENCY (A.U.)
5.0
3.0
1.0
0.5
0.3
360
380
400
420
440
460
480
WAVELENGTH (nm)

APPARATUS FOR MEASURING THE AUTOFLUORESCENCE OF THE CORNEA OF AN EYE

FIELD OF THE INVENTION

This invention relates to an apparatus for measuring the autofluorescence of the cornea of an eye, comprising means for substantially tangentially illuminating the cornea, means for receiving the autofluorescent radiation generated in the cornea by this illumination, and means for processing the measured autofluorescent radiation.

BACKGROUND OF THE INVENTION

Such an apparatus is known from Italian patent application IT-94.501.069.

Apparatuses for measuring the autofluorescent radiation of the cornea of an eye are used in screening diabetes patients for diabetic retinopathy. Diabetic retinopathy is one of the moat important causes of blindness in the Western world and its timely detection can contribute to delaying or even preventing blindness in patients by administering laser therapy. Recent studies have shown that the autofluorescence of the corneal tissue in certain wavelength regions increases considerably with the severity of diabetic retinopathy. By other conventional methods, diabetic retinopathy and its progression are difficult to detect. The advantage of measuring corneal autofluorescence is that the cornea is readily accessible for examination and that the amount of corneal autofluorescence is not or only slightly age-dependent.

In the apparatus known from the above-mentioned Italian patent application, the above-described insight is already utilized in an attempt to measure corneal autofluorescence. In practice, however, this known apparatus has proved to be insufficiently sensitive and accurate, inter alia because the autofluorescence of the crystalline lens located behind the cornea is many times greater than the autofluorescence of the cornea itself, so that in the absence of measures to suppress lenticular autofluorescence, the measurement is not sufficiently accurate. An additional problem is that lenticular autofluorescence is highly age-dependent, starting at near-zero at birth and increasing to 50 times the value of corneal autofluorescence at the age of 90. Further, the spread of lenticular autofluorescence among individuals of the same age is large. Accordingly, lenticular autofluorescence cannot be simply eliminated as a fixed interference factor, since its value is unknown.

The object of the invention is to improve the known apparatus, such that, in a simple and yet sufficiently accurate manner, corneal autofluorescence can be measured, while yet the apparatus is of simple and robust construction. In addition, the object of the invention is to provide an apparatus that is inexpensive to manufacture and simple to operate, which is of great importance especially for use in developing countries.

SUMMARY OF THE INVENTION

To that end, the invention provides an apparatus of the above-mentioned type, characterized in that the means for tangentially illuminating the cornea comprise at least one light source which radiates blue light and at least one filter which transmits at least a part of the blue light in a light path to the cornea, that the means for receiving the autofluorescent radiation generated in the cornea comprise at least one filter which transmits green light, that the apparatus further comprises a light source for causing the pupil to contract, as well as switching means for switching on, in succession, the blue light source for a first predetermined period and then the light source for causing the pupil to contract for a second predetermined period, and for repeating this cycle a number of times.

It is noted that EP-A-776628 discloses an apparatus for eye measurement which is alleged to make it possible to perform a variety of types of eye measurements, including measuring the autofluorescence generated by the cornea. This publication, however, is directed to measuring autofluorescence values to determine whether or not a patient has diabetes. The device described, however, is not accurate enough to determine whether in a patient diabetic retinopathy occurs, i.e., whether in a patient already known to have diabetes, the diabetes also affects the cornea. The differences in corneal autofluorescence values to be measured for this purpose are so small that the known device is not suitable for that. Moreover, the known device is large and costly, while, further, use is made of a line-shaped light ray for exciting the cornea, instead of a light beam as in the invention. Nor does the publication mentioned disclose the provision of separate light sources which keep the pupil contracted prior to measurement, but also during measurement. Only an additional light source for focusing the eye is described.

The invention will be further elucidated hereinafter on the basis of an exemplary embodiment, with reference to the drawings, wherein:

DETAILED DESCRIPTION OF THE PREFERRED

Figure 1:
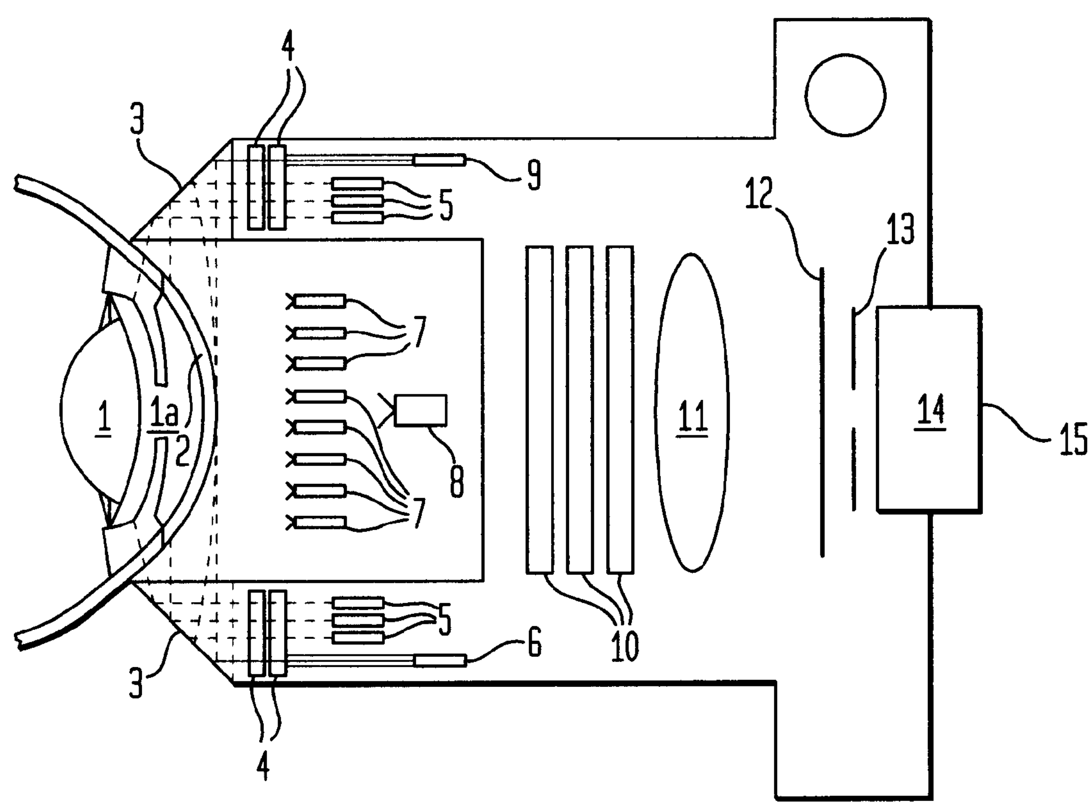
FIG. 1 is a diagrammatic side elevation of thy apparatus according to the invention, positioned in front of an eye.

FIG. 1 shows, in side elevation, an apparatus according to the invention. Also schematically represented, for the sake of clarity, is an eye, with a lens 1, a pupil 1*a* and a cornea 2. The apparatus is intended for measuring the autofluorescence of the cornea 2 of such an eye and, to that end, comprises a number of light sources 5, 6, 7, 8 and 9, and a number of optical and filter elements 3, 4, 10, as well as a receiving means for measuring the fluorescent radiation of the cornea, which receiving means, in the exemplary embodiment, comprises a camera 11, 12, 13 and a photomultiplier 14.

The light sources are preferably all formed by one or more light-emitting diodes, which radiate different colors of light. Hereinafter, these light-emitting diodes will be referred to as LEDs. Provided are six blue light-emitting LEDs 5, sixteen green light-emitting LEDs 7, an infrared light-emitting LED 6 and a red light-emitting LED 8, which is positioned centrally in front of the eye.

A blue light beam of the LEDs 5 is transmitted via a blue excitation filter 4 and an internally totally reflective prism 3, tangentially to the cornea 2, as indicated in the figure by dotted lines. The blue light beam has an apical angle of 10–60°, preferably 20–40°, and is, for instance, symmetrical with respect to the central dotted line.

Figure 2A:
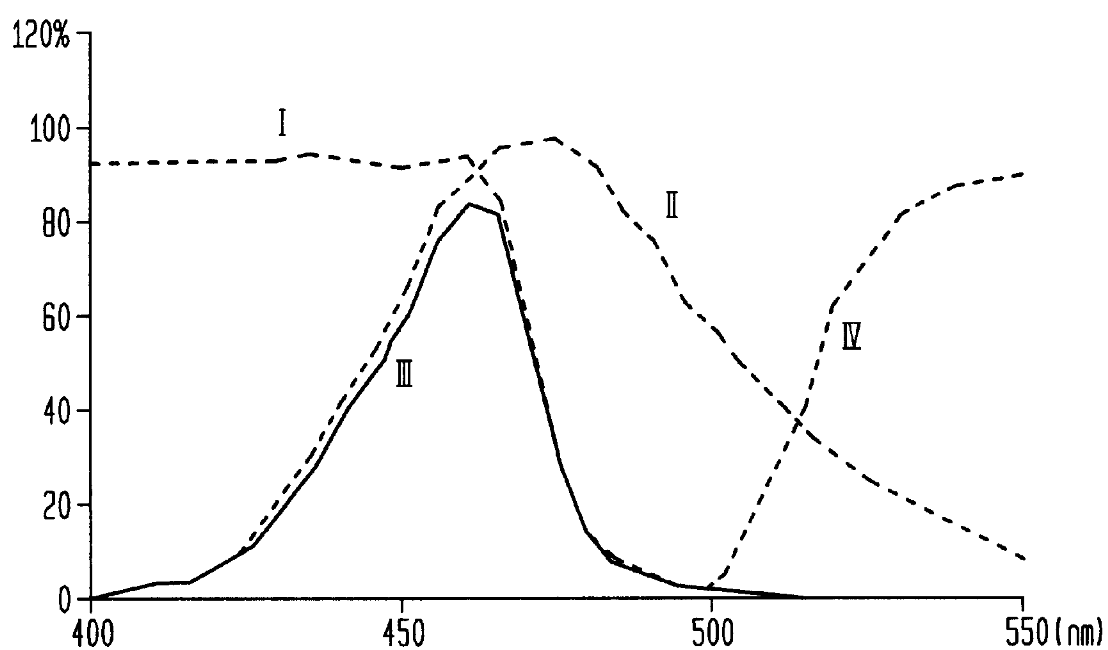
FIG. 2*a* is a graphic representation of, respectively, the intensity of the blue illumination source before and after a filtering operation, the transmittance of the filter for the illumination source, and the transmittance of the fluorescence filter for measuring the autofluorescence of the cornea.

FIG. 2*a* shows a graph in which curve II indicates the intensity of the blue LEDs 5 as a function of the wavelength in nm. Curve I gives the transmissivity of the blue excitation filter 4, likewise as a function of the wavelength, and curve III represents the amount of light transmitted by the filter 4 and passed to the cornea 2.

The blue light according to curve III, which reaches the cornea tangentially, leads to autofluorescence of the cornea, and the autofluorescent radiation thereby generated is transmitted via filter 10, with a transmittance indicated by curve IV in FIG. 2. It will be clear that the emission through this filter 10 is highly dependent on the properties of the cornea under examination.

The task of the blue LEDs 5 is therefore to excite the autofluorescence of the cornea, the chief object of the invention. The blue filters 4 and the filters 10, which are green and transmit the autofluorescent radiation to the camera, have the purpose of separating the spectra of the blue excitation light and the green autofluorescent radiation as much as possible, in order that no blue light can reach the detection circuit. In practice, a series connection of 2 or 3 filters has proved to be sufficient to realize the desired separation of the spectra.

The purpose of the other LEDs 6, 7 and 8 is to enable the measurement to be performed simply and accurately and to prevent interference signals to a far-reaching extent. Their function will be discussed in the following.

The purpose of the infrared LED 6 is to make it possible to accurately determine the position of the apparatus according to the invention with respect to the eye under examination in the x-direction. To that end, LED 6 cooperates with an infrared detector 9. The light of the LED 6 is transmitted via the prism 3 and, line-shaped, directed tangentially to the eye. If the apparatus is correctly placed with respect to the eye, the infrared light passes just in front of the cornea, without being absorbed by it. The infrared light can then, via the opposite prism 3 reach the infrared detector 9. Infrared detector 9 can, for instance, be connected to an electronic circuit which produces a warning signal as long as the infrared light from the LED 6 reaches the detector 9, this signal being interrupted when the detector 9 receives no or insufficient light. Partly because the light of the infrared LED 6 and that of the blue LEDs 5 follow the same light path, mispositioning is precluded. In this way, a correct positioning with respect to the eye can be obtained readily and fast.

The purpose of the green LEDs 7 is to generate such an amount of light that the eye's pupil 1*a*, which is located in front of the lens 1, contracts as far as possible. This is of great relevance to sufficiently suppress fluorescence of the lens 1, which is much stronger than the autofluorescence of the cornea, in order not to introduce any measuring errors. In addition, the green LEDs can illuminate the eye which, via the filters 10, can be viewed by the viewer of the camera, so that the operator can position the camera properly in the y- and z-direction relative to the eye.

The red LED 8, which is arranged centrally, has three different functions.

A first important purpose of the red LED 8 is to ensure that the pupil remains as small as possible during the measurement, when, as will be explained below, the green LEDs 7 are off. When the pupil is as narrow as possible, the contribution of lenticular autofluorescent radiation to the measured value is at a minimum. Since the light yield in a red LED can be many times greater than that of green LEDs, a single red LED can suffice. During the setting phase, the power of the red LED is lower than during the measuring phase.

Secondly, the red light 8 functions as a focusing point for the patient to be examined, so that he himself cooperates towards the proper positioning of the eye relative to the apparatus in the y- and z-directions.

A third function of the red LED 8 is its function as mechanical shielding element to block any fluorescent radiation which may yet have been emitted by the lens 1 via the pupil.

The autofluorescent radiation of the cornea reaches via the filter 10, which is a green fluorescence filter, the lens 11 of a camera, which further comprises, conventionally, a shutter 12, a diaphragm 13 and, instead of a film, a photomultiplier 14. The photomultiplier 14 converts the received fluorescent radiation, in a manner known per se, into an electrical signal which is a measure for the amount of radiation reaching the photomultiplier 14.

The output signal of the photomultiplier 14, 15 in FIG. 1 is applied to an electronic processing circuit, which further comprises the control electronics for controlling the on/off cycles of the various LEDs.

Figure 2B:
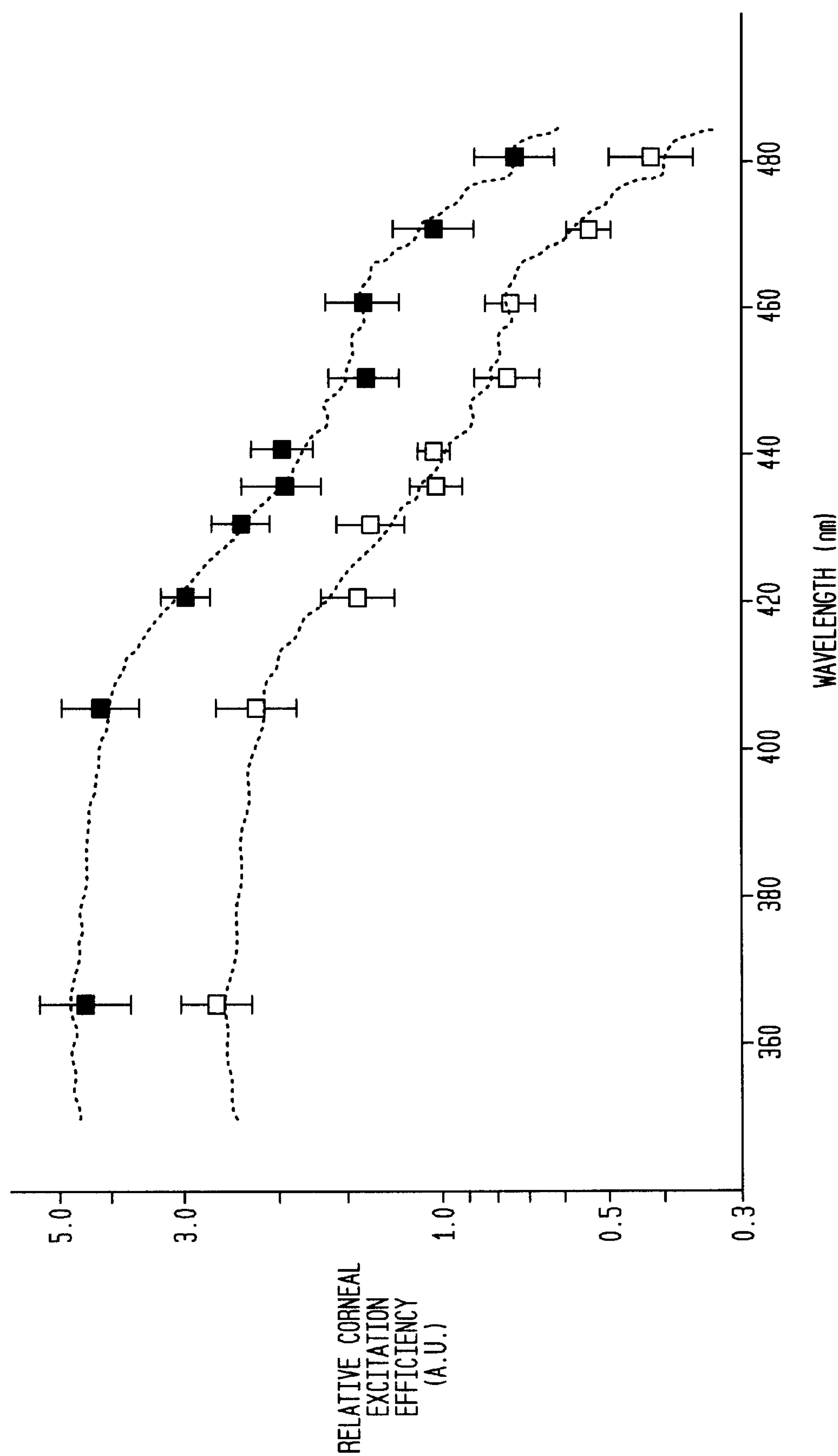
FIG. 2*b* is a graphic representation of measuring results obtained with an apparatus according to the invention.

FIG. 2*b* shows a number of measuring results obtained with the apparatus according to the invention. The graph of FIG. 2*b* plots, along the horizontal axis, the wavelength of the light used for generating the autofluorescence of the cornea, ranging from 360 to 480 nm, i.e., from ultraviolet (<400 nm) to blue (≈400–500 nm), while the measured autofluorescence is plotted along the vertical axis. Ultraviolet is not suitable for in vivo measurement in view of the risk of damage to the eye. In the figure, open cubes represent the measuring results in healthy test subjects at various wavelengths, and solid cubes represent the measuring results in test subjects having diabetic retinopathy. It appears from the figure that in the range of the blue light, in particular in the wavelength range of 400–500 nm, properly useful measuring results were obtained to make a clear distinction between healthy and ill subjects.

Figure 3:
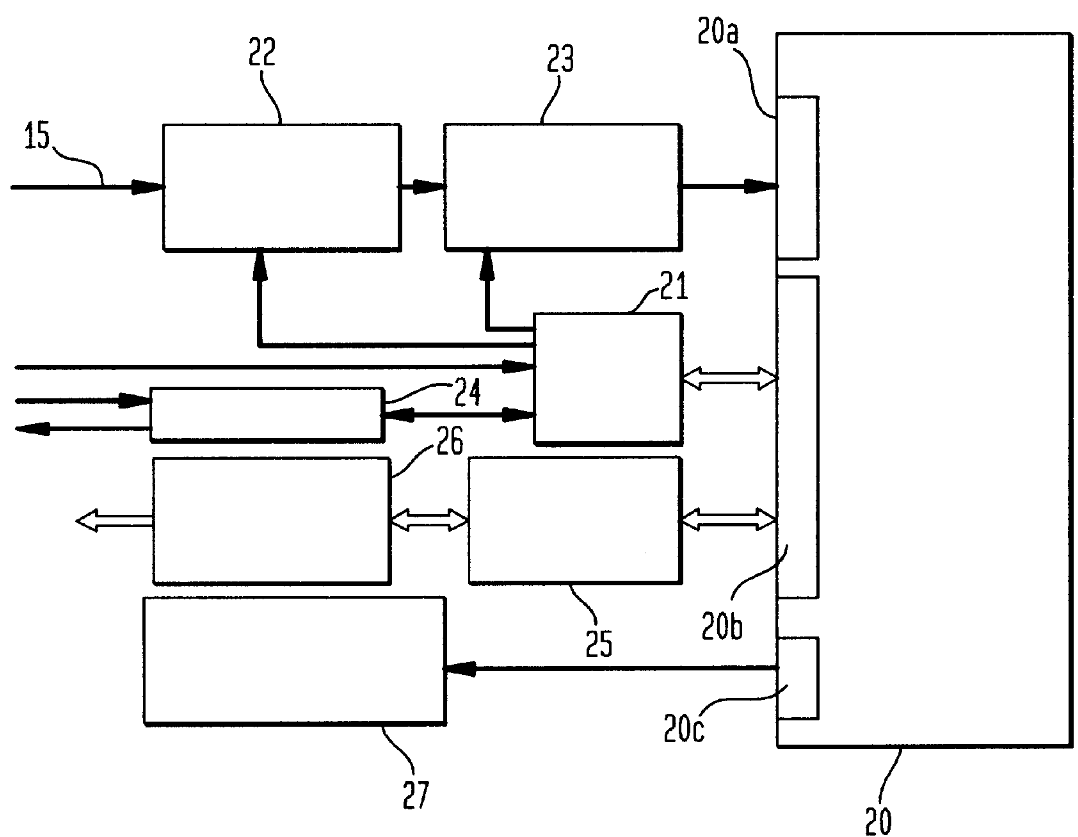
FIG. 3 is a block diagram of the apparatus according to the invention.

FIG. 3 shows a block diagram of the control and processing circuit. The circuit is built up around a microprocessor 20. The output signal of the photomultiplier 14, 15 is applied to an integrator 22 controlled by the microprocessor 20 via the input/output buffer circuits 21. The output signal of the integrator 22 is applied via a sample-and-hold circuit 23 to an A/D converter 20*a* of the microprocessor 20.

Via the buffer circuits 21, which are connected with the digital input/output port 20*b* of the microprocessor, the microprocessor 20 also controls the infrared amplifier 24 for positioning the apparatus with respect to an eye in the x-direction, using the infrared LED and the infrared detector. The digital input/output ports 20*b* of microprocessor 20 further control, via suitable control buffer circuits 25, the control circuit 26 for the various LEDs or groups of LEDs, as will be further explained below.

Finally, to the serial port 20*c* of the microprocessor 20, a display 27 is connected which, after a number of measuring cycles, displays numerically the mean measured value of the corneal fluorescence.

Figure 4:
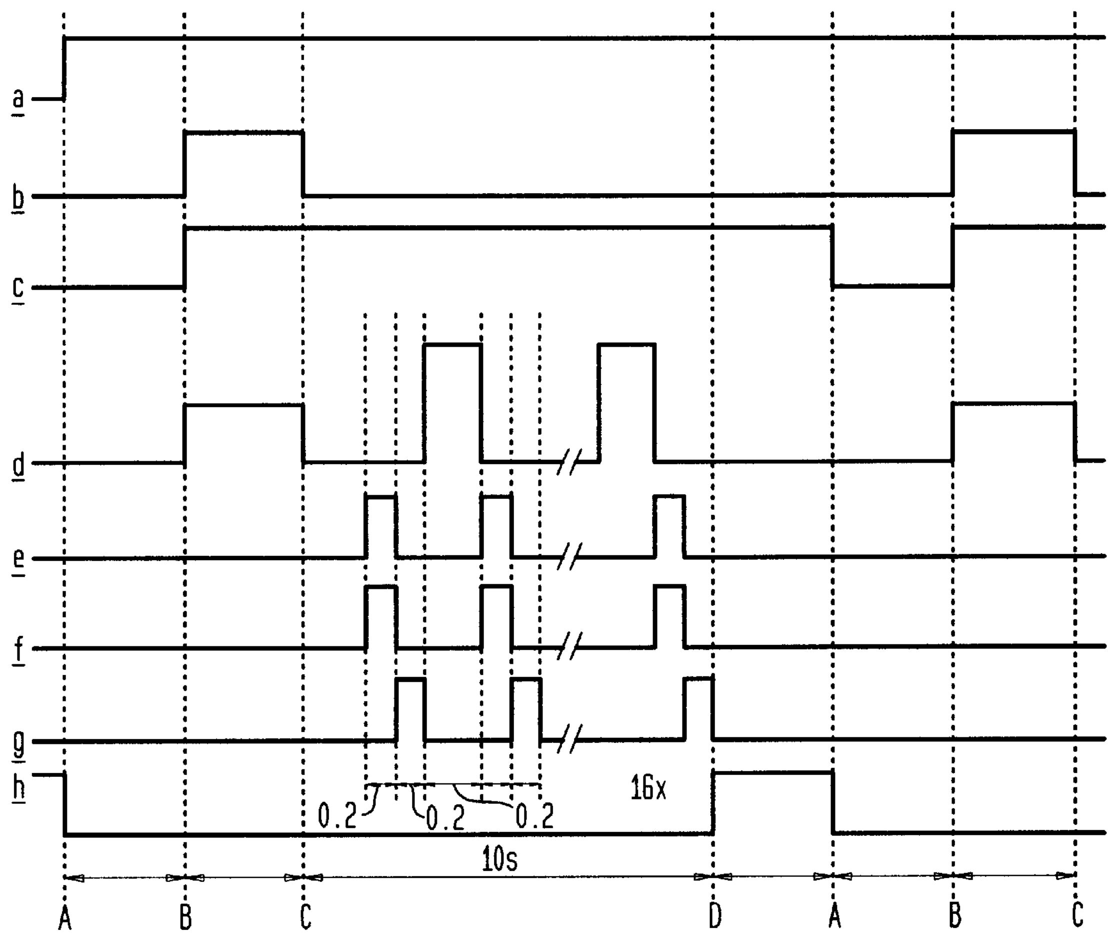
FIG. 4 is a time diagram of the activation of the various parts of the apparatus according to the invention.

The measuring cycles shown in FIG. 4 are optimized, on the one hand, to realize a highest possible signal-to-noise ratio and, on the other hand, to minimize the undesired contribution of lenticular fluorescence to the measuring signal.

FIG. 4 plots time along the horizontal axis, and along the vertical axis, on the lines a–h, the active or passive state of a part of the apparatus, the active state being indicated by a "high" signal and the inactive state by a "low" signal.

On line a, at time A, the supply of the apparatus is activated. In the period A-B, the apparatus, using the microprocessor 20, checks if the various LEDS function properly by switching them on and off alternately.

At time B, if the check during period A-B has not revealed any errors, begins the setting cycle of the apparatus with respect to an eye to be examined.

During the period B-C, both the green LEDs 7 (line b), the infrared LED 6 (line c), and the red LED 8 (line d) are activated. The red LED a which, in this phase, functions only as focusing point, is driven with a low current, so that its light yield is low and is not a nuisance to the patient under examination.

During period B-C, the investigator can position the apparatus correctly with respect to the eye in the y- and z-directions with the aid of the green LEDs 7 via the viewer of the camera, and in the x-direction with the aid of the signal of the infrared LED 6 and the associated detector 9.

At time C, the shutter of the camera is activated and the actual measuring cycles begin. First, the green LEDs 7, which have been used for positioning, are switched off, as is the red LED 8. Then the blue LEDs 5 are activated for a predetermined period, for instance 0.2 sec. as shown on line e. During these 0.2 seconds, the fluorescent radiation received by the photomultiplier is integrated (line f). A period of 0.2 seconds is too short for the pupil to open to a significant extent.

After these 0.2 seconds, the output signal of the driven integrator 22 (FIG. 3) is applied to the sample-and-hold circuit 23 and converted into a digital measuring signal by the A/D converter of the microprocessor 20. Then the integrator 22 is reset to zero by the microprocessor 20 via a FET switch, and for 0.2 seconds, with the blue LEDs 5 switched off, the background radiation is measured in exactly the same manner (line g). The signal determined by the integrator 22, the sample-and-hold circuit 23 and the A/D converter in the microprocessor, which now represents the background radiation, is subtracted from the measured signal is of the fluorescent radiation to thereby obtain a measuring signal stripped of background radiation. To prevent the pupil dilating, after measuring the background radiation, the red LED 8 is driven at a high current to obtain a high light intensity. After switching off the red LED 8, again the blue LEDs are activated, the background radiation is measured, and the red LED is activated. Measuring the background radiation and activating the red LED 8 each time after activation of the blue LEDs 5 in each measuring cycle according to the invention prevents an interfering contribution of the fluorescence of the crystalline lens and of the background radiation.

The above cycle of switching on blue LEDs, measuring background radiation and switching on the red LED is traversed a total of sixteen times, whereafter a stop signal is produced at time D.

It will be clear that the on- and off-times of the various LEDs and the number of cycles are adjustable, such that an optimum measuring result is obtained.

At the end of the measurement, the following data are available: the mean fluorescence value and the standard deviation for the individual cycles, as well as the maximum value of the background signal. This last measuring value can be used to adjust the background lighting in the space where the examination is taking place, such that no saturation of the photomultiplier 14 occurs.

What is claimed is:

1. An apparatus for measuring the autofluorescence of the of the cornea of an eye, comprising means for substantially tangentially illuminating the cornea, means for receiving the autofluorescent radiation generated in the cornea by this illumination, and means for processing the measured autofluorescent radiation, wherein the means for tangentially illuminating the cornea comprise at least one light source which radiates blue light and at least one filter which transmits at least a part of the blue light in a light path to the cornea, the means for receiving the autofluorescent radiation generated in the cornea comprise at least one filter which transmits green light, the apparatus further comprises a light source for causing the pupil to contract, as well as switching means for switching on, in succession, the blue light source for a first predetermined period, and then the light source for causing the pupil to contract for a second predetermined period, and for repeating this cycle a number of times.

2. An apparatus according to claim 1, wherein the means for substantially tangentially illuminating the cornea radiate a light beam which is symmetrical with respect to an axis of illumination and includes, around that axis, an angle of 10–60°, preferably 20–40°.

3. An apparatus according to claim 1, further comprising a light source which radiates red light, which serves as a light source for causing the pupil to contract and as a focusing point.

4. An apparatus according to claim 1, wherein the light transmitted by the blue light filter is directed at the cornea through an internally totally reflective prism.

5. An apparatus according to claim 1, having at least one blue light source is arranged on opposite sides of a patient's eye.

6. An apparatus according to claim 1, having at least one light source radiating green light is arranged between the green light filter and a patient's eye.

7. An apparatus according to claim 1, wherein the apparatus comprises an infrared light source on one side and an infrared detector on the other side to enable positioning of the apparatus with respect to the eye.

8. An apparatus according to claim 7, wherein a plurality of light sources radiating green light are arranged in a circular configuration opposite the eye.

9. An apparatus according to claim 1, wherein the light sources are light-emitting diodes.

10. An apparatus according to claim 1, wherein the first predetermined period is approximately 0.2 seconds.

11. An apparatus according to claim 6, comprising means for switching on the green light source prior to switching on the red and blue light sources.

12. An apparatus according to claim 11, wherein the switching means also switches on the red light source for the same period as for the green light source, with power during the subsequent periods.

* * * * *

UNITED STATES PATENT AND TRADEMARK OFFICE
CERTIFICATE OF CORRECTION

PATENT NO. : 6,611,704 B1
DATED : August 26, 2003
INVENTOR(S) : Jasper Anton van Best and Franco Docchio It is certified that error appears in the above-identified patent and that said Letters Patent is hereby corrected as shown below:

Title page,
Item [22], PCT Filing Date, "October 9, 1998" should read -- September 10, 1998 --.

Signed and Sealed this

Second Day of March, 2004

JON W. DUDAS
*Acting Director of the United States Patent and Trademark Office*